United States Patent [19]

Seubert et al.

[11] Patent Number: 4,946,829

[45] Date of Patent: * Aug. 7, 1990

[54] PROCESS AND HUMINATE FRACTION

[75] Inventors: Bernhard Seubert, Edingen-Neckarhausen; Werner Fickert, Mannheim; Ulrich Spitaler, Freinsheim, all of Fed. Rep. of Germany

[73] Assignee: Rutgerswerke AG, Fed. Rep. of Germany

[ * ] Notice: The portion of the term of this patent subsequent to Apr. 17, 2007 has been disclaimed.

[21] Appl. No.: 193,957

[22] Filed: May 13, 1988

[30] Foreign Application Priority Data

Oct. 29, 1987 [DE] Fed. Rep. of Germany ....... 3736623

[51] Int. Cl.$^5$ .................... A61K 31/00; C07C 33/00
[52] U.S. Cl. ........................... 514/22; 514/730; 568/715; 210/649; 536/121
[58] Field of Search ............... 514/60, 22, 730; 568/715; 210/649; 536/121

[56] References Cited

U.S. PATENT DOCUMENTS

| | | | |
|---|---|---|---|
| 3,238,100 | 3/1966 | Meyer et al. | 514/60 |
| 4,728,642 | 3/1988 | Pawelchak et al. | 514/60 |
| 4,843,105 | 6/1989 | Rerschl et al. | 435/182 |

OTHER PUBLICATIONS

Lakatos et al., *Chemical Abstracts,* vol. 88 (5), Jan. 30, 1978; 88:36425y, p. 405.
Zeng et al., *Chemical Abstracts,* vol. 103 (13), Sep. 30, 1985; 103:98707d, p. 56.
Wang et al., *Chemical Abstracts,* vol. 97 (25), Dec. 20, 1982; 97:208076q, p. 70.

*Primary Examiner*—Ronald W. Griffin
*Assistant Examiner*—Pamela S. Webber
*Attorney, Agent, or Firm*—Bierman and Muserlian

[57] ABSTRACT

A process for the preparation of a low molecular weight alkali metal or ammonium huminate fraction comprising stirring an aqueous suspension of a humic containing material while adding an alkaline substance without exceeding a pH of 7, allowing the solids to settle from the suspension, centrifuging the solid free solution and subjecting the solution to ultrafiltration to obtain a low molecular weight alkali metal or ammonium huminate fraction and an improved method of healing wounds.

11 Claims, No Drawings

PROCESS AND HUMINATE FRACTION

STATE OF THE ART

Healing properties for humic acids or humic substances such as those occurring in marshes, peat, colored clays or humic containing water are known [Ziechmann, Therapiewoche, Vol. 28 (1978), p. 1199–1211] but humic acids and their salts are considered to be parenterally toxic [Kuhnert et al., Arch. Exper. Vet. Med., Vol. 36 (1982), p-169-177]. Therefore, humic substances have usually been used only as mud baths and in veterinary medicine.

In copending U.S. patent application Ser. No. 162,741 filed Mar. 1, 1988, an alkali metal huminate is disclosed with a substantially lower parenteral toxicity with good healing effects. The said huminates have an average molecular weight of 1000 g per mole with a range of 300 to 1500 g/mol. The alkali metal huminate fraction is prepared so that humic substance-containing products are slurried in an alkali metal or ammoniacal aqueous solution with the resulting solution being separated from coarse solid materials and freed by centrifugation of fine solid matter and high-molecular huminates, the resulting solution being neutralized and buffered at a pH value in the range of 6.2 to 7.2, and again purified by centrifugation to obtain from this solution a low-molecular weight fraction. This method is relatively elaborate, tedious, and ill-suited for the cost-efficient preparation of huminates. In addition, the product due to the repeated pH variation contains additional undesirable salts. Furthermore, through the pH shift, changes in the structure of the humic substances can occur and, consequently, losses in the yield of the low-molecular weight fraction.

OBJECTS OF THE INVENTION

It is an object of the invention to provide an improved process for the preparation of low-molecular weight alkali metal or ammonium huminates.

It is another object of the invention to provide an improved composition and method for healing wounds.

These and other objects and advantages of the invention will become obvious from the following detailed description.

THE INVENTION

The novel process of the invention for the preparation of a low-molecular weight alkali metal or ammonium huminate fraction comprises stirring an aqueous suspension of a humic containing material while adding an alkaline substance without exceeding a pH of 7, stirring the suspension until the pH is 7, allowing the solids to settle from the suspension, centrifuging the solid free solution and subjecting the solution to ultrafiltration to obtain a low molecular weight alkali metal or ammonium huminate fraction. The process is simple, economical and is free of additional salts and changes in the humic substances which occurs with pH changes.

The desired low-molecular weight huminate fraction can be obtained in a manner which can be carried out cost-effectively on a commercial scale from humic substance containing products if these are suspended in water and mixed with an alkaline-acting substance for a length of time in that the pH value of 7 is not exceeded. After a relatively brief stirring time of 30 to 180 minutes, the solid substances of the suspension are settled out, and the solution largely free of solid matter is separated from the settled out products through drawing off or decanting. This solution is then centrifuged and subjected to ultrafiltration to obtain a sterile, ready to use solution of effective agents with a content of huminates of 2 to 10 percent by weight. This solution is stable, i.e, the changes observed per se with huminate solutions in the sense of further polymerization are not observed even after prolong storage at increased temperatures.

Starting products for the huminates of the invention are all humic substance-containing products such as, for example, peat, marsh, coal, colored clays or humic substance-containing water or their humus slurry. These humic substance-containing materials preferably are high-humic substance substrates having a content of at least 5, maximally approximately 50% humic acids. They are slurried in water and, while being stirred, carefully mixed with an alkaline-acting substance so that the pH value of the reaction mixture is in the range between 6 and 7 and under no circumstances exceeds the value 7. The preferred pH range is 6.3 to 6.5. An aqueous solution of an alkali metal hydroxide can serve as the alkaline substance and the salt of an alkali metal is obtained through hydrolysis reacting alkaline with a weak acid or that of an amine or of ammonia, but also amines or ammonia introduced directly into the reaction mixture. The preferred alkaline-acting substance is potassium carbonate, which is used preferentially as 10% solution.

The amount of alkaline substance is not critical as long as the pH value of 7 of the reaction mixture is not exceeded. On the other hand, attempts are made to bring a maximum amount of huminate into solution to achieve as high a yield as possible.

According to the invention, therefore, two rapid methods have been developed to determine the optimum amount of alkaline-acting substance: (1) the humic substance-containing product is pre-dried before forming the suspension in de-ionized water (approximately by drying for 8 to 12 hours in a drying oven at 80 to 85° C.) and then is ground finely and mixed thoroughly. This ensures that a highly homogeneous standardized product for use is generated. Several 100 g samples of this product are then dried for approximately 15 to 20 hours at 120 to 140° C. and the remaining residue is determined as dry mass. The solid matter content of the dry mass, depending on the kind of humic substance-containing material used is in the range of 50 to 75% of the standardized product for use. According to the invention, 50 to 100 mol of an alkaline-acting substance is used per 100 g of dry mass.

(2) The second possibility consists in titrating a sample of the standardized product and the amount determined is the amount of alkali which is required to obtain the last point of change before pH 7. This is the amount of alkali metal to be used in the preparation method. The corresponding multiple of this amount of alkali metal is added, while the pH is controlled extremely precisely, to a slurry of the standardized product in de-ionized water. Then, the solution is stirred for approximately another one half to three hours until a constant pH is reached. This lies preferentially in the range of 6.3 to 6.5. At this point, the mixture is allowed to settle for one to two hours and the supernatant dark brown solution is separated carefully from the settled slurry. The so obtained, largely solid matter-free solution is freed further in a centrifuge up to 8,000 to 10,000 × g from undissolved particles. The clarified solution is subsequently subjected to ultrafiltration, with the pore range of the filters being in the range of 50,000 to 1,000,000 Dalton.

The obtained solution has a content of low-molecular weight huminate of 2 to 10 percent by weight and it can be used directly or through careful removal of water, possibly by freeze-drying, dried to form a solid substance with at least 4% residual moisture. This is a further advantage of the method of the invention in which the low-molecular weight huminates contain no fraction of medium-molecular weight huminate substances.

Huminates prepared by older methods still contain a slight amount of a medium-molecular weight fraction and can only be concentrated to higher concentrations. However, upon further water removal, they are irreversibly destroyed even with exceedingly gentle processes. The solid material obtained by the invention containing 4% residual moisture or as a concentrated aqueous solution are stable. In stability tests after 60 days of alternating stress at 56 and 4 C every 12 hours, no changes of the parameters content, pH value, oxidation-reduction potential and microdialysis test was noted beyond random fluctuations.

To determine the approximate molecular weight, a sample of the solution is subjected to electrophoresis and on the basis of the electrophoretic migration rate for the huminates, an average molecular weight of 1,000 with a range from 300 to 1500 is determined. Toxicity tests indicated that the low-molecular weight huminates have low toxicity and it was found that they also show the already observed healing effect, particularly in wound healing. For many applications, however, an aqueous solution is unsuitable and the effective agent is required in water-free form.

In U.S. patent application Ser. No. 162,203 filed Mar. 1, 1988, a method for the preparation of a water-free application form of the low-molecular weight huminates is described in which an aqueous solution of these huminates is mixed with 0.2 to 5 fold volume of an inorganic carrier material and the obtained mixture is dried. This method can be integrated into the preparation of the invention. Examples of inorganic carrier material are aluminum oxide, titanium dioxide, silicon dioxide, particularly highly dispersed silisic acid or clay. Preferably montomorilonite or bentonite can be moistened with the solution obtained through ultrafiltration and the obtained substance can be dried. It has proven particularly useful to mix 10 to 100% of the inorganic carrier material, relative to the dry content of the solution, with the solution and to dry the resulting suspension continuously in a thin layer evaporator. A storage-stable, pourable powder is obtained which alone or in combination with auxiliary materials can be used as a powder, in sprays or in water-free salves.

Moreover, a low-molecular weight huminate fraction which has been dried to a content of 4 to 8% residual moisture, can be made to form a stable, pourable application form by being finely ground with commercially available sugars and starches or modified starches. Relative to the effective substance amount, fine grinding with 20 to 200% sugar or starch content is advisable to obtain a storage-stable pourable powder, which alone or in combination with other auxiliary substances can be used in appropriate medicinal forms, preferably as powder, in sprays, salves or adhesive paste.

The novel method of treating wounds of warm-blooded animals, including humans, comprises topically applying to a wound an effective amount of a low-molecular weight alkali metal or ammonium huminate of the invention.

In the following examples there are described several preferred embodiments to illustrate the invention. However, it should be understood that the invention is not intended to be limited to the specific embodiments.

EXAMPLE 1

20 kg of humus slurry were predried in a drying oven for 12 hours at 80° C. and then were ground in a mill into 1 to 3 mm large particles and homogenized and standardized. A 1 g sample of the standardized humus slurry was slurried in distilled water and titrated with 0.1 M sodium hydroxide and the pH changes were measured potentiometrically. After addition of 6 9 ml of 0.1 M sodium hydroxide, a point of change in the range of pH 6 to 6.5 was observed. For that reason, 0.69 mmol of sodium hydroxide per g were considered to be optimum alkali amount for this standardized humic substance-containing product.

In a stirring unit, 10 kg of standardized humus slurry were slurried in 100 liters of distilled water and while being stirred, 117 g of gaseous $NH_3$ were slowly introduced into the suspension. The pH value of the suspension, which during this process was continuously controlled, increased from original 3.9 steadally to 6.3. Beginning with this value at the latest, the addition of the ammonia was throttled so that the pH value remained in the region of 6.3 to 6.5, i.e. the quantity of the added alkaline-acting substance corresponded to that used in the same period in the neutralization of the complex humic substances. Following the addition of $NH_3$ which was completed after 70 minutes, stirring continued for an additional one hour. The stirrer was then switched off and the suspended solid matter settled as slurry at the bottom of the vessel. The supernatant brown solution was decanted and centrifuged directly in a separator at 9,000 × g. The resulting purified solution was subjected to ultrafiltration with an ultrafilter of pore width 100,000 D to obtain a dark brown solution with a 2.1% content of an ammonium huminate fraction with an average molecular weight of 1,000 and a range of 300 to 1500.

EXAMPLE 2

20 kg of healing clay were predried in a drying oven for 12 hours at 80° C. and then ground into 1 to 3 mm large particles in a mill and homogenized and standardized. A 100 g sample of the standardized healing clay was dried rigorously for 16 hours at 130° C. and, then the weight loss was determined. On this basis, a solid matter content of 69% by weight was determined.

In a stirring unit container, 10 kg of standardized healing clay were slurried in 100 liters of distilled water resulting in a pH value of 3.5. While stirring and continuously checking the pH of the suspension, 7.630 g of a 10% potassium carbonate solution (corresponding to 5.520 mmol of $K_2CO_3$ or corresponding to 80 mmol of $K_2CO_3$/100 g of rigorously dried healing clay) were slowly added to the suspension so that a pH value of 7 was not exceeded.

After the potassium carbonate addition which was completed after 60 minutes, stirring was continued for another hour, in the process of which a constant pH value of 6.5 was established. Subsequently, the stirrer was switched off and the suspended solid matter settled as a slurry at the bottom of the vessel. The supernatant brown solution was decanted off and centrifuged directly in a separator at 9,000 × g. The purified solution obtained was subjected to an ultrafiltration with an ultrafilter of pore width 100,000 to 250,000 D to obtain a dark brown solution with a 3.2% content of a potassium huminate fraction having an average molecular weight of 1,000 and a range of 300 to 1,500.

EXAMPLE 3

32 g of titanium dioxide powder were suspended in 5 liters of the potassium huminate solution obtained in Example 2 and the obtained suspension was evaporated continuously in a thin layer evaporator until a solid was obtained. The product obtained was grey and pourable, was stable up to 130° C. and the effective agent was again isolated after contact with water.

EXAMPLE 4

With the solutions (1) and (2) obtained in Examples 1 and 2, the investigations described below were carried out and the listed results were obtained.

Toxicity

After injecting the 1% solution into experimental animals (mice), the following values for $LD_{50}$ are obtained.

|  | Solution (1) | Solution (2) |
| --- | --- | --- |
| subcutaneous | 1292 (mg/kg) | 1136 (mg/kg) |
| intraperitoneally | 853 | 784 |
| intraveinously | 676 | 722 |

Stability:

In the stability test after 60 days of alternating from 56 to 4° C. every 12 hours, no changes of the parameters content, pH value, oxidation-reduction potential, and microdialysis test outside of random fluctuations were detected.

Healing efficacy:

Fibroblast test

A culture of L-cells (mouse fibroblasts) was treated with trypsin and brought into suspension with 50 ppm of low-molecular alkali metal huminate (solutions of Examples 1 and 2). The culture was incubated for 48 hours at 37° C. using a commercially available nutrient medium. In a comparison test and parallel to it, an analogous culture without alkali metal huminate was incubated in the same way. Then, the number of viable cells in both cultures was determined and in the cultures mixed with the low-molecular alkali metal huminates, the number of viable cells was 30% higher than in the comparison culture.

Healing of wounds

With a microdermatome, superficial wounds of a size of 50 mm² involving only the upper epithelial layers were produced in 2 lots of 10 hairless mice. In ten of these mice, the wound was wetted in each instance with a 1% solution (from Example 1 and 2) and the other mice remained untreated. During the observation time span of 7 days, the following was observed compared to untreated mice. In the treated experimental animals the wound area decreased more rapidly, the wound dried earlier, granulation occurred earlier, and the wound became clean sooner. Overall, healing occurred 2 to 3 days earlier than in the control animals.

Various modifications of the compositions and method of the invention may be made without departing from the spirit or scope thereof and it should be understood that the invention is intended to be limited only as defined in the appended claims.

WHAT WE CLAIM IS:

1. A process for the preparation of a low molecular weight alkali metal or ammonium huminate fraction comprising stirring an aqueous suspension of a humic containing material while adding an alkaline substance without exceeding a pH of 7, stirring the suspension until the pH is 7, allowing the solids to settle from the suspension, centrifuging the solid free solutions and subjecting the solution to ultrafiltration to obtain a low molecular weight alkali metal or ammonium huminate fraction.

2. The process of claim 1 wherein the humic containing material is predried before suspension.

3. The process of claim 1 wherein the alkaline substance is selected from the group consisting of alkali metal hydroxides, alkali metal carbonates and ammonia.

4. The process of claim 1 wherein the alkaline substance is potassium carbonate.

5. The process of claim 1 wherein the pH is maintained between 6.3 and 6.5.

6. The process of claim 1 wherein the amount of alkaline substance added is 50 to 100 mmol of alkaline substance per 100 g of dried humic containing material.

7. The process of claim 1 wherein the solid-free solution is centrifuged at 8000 to 10,000 × g.

8. The process of claim 1 wherein the ultrafilter has a pore diameter of 50,000 to 1,000,000 Dalton.

9. The process of claim 1 wherein the solution from ultrafiltration is mixed with 10 to 100% by weight of an inorganic carrier material based on the solid matter content of the solution and the mixture is dried to a pourable product.

10. The process of claim 9 wherein the inorganic carrier is titanium dioxide powder.

11. The process of claim 1 wherein the solution from ultrafiltration is dried to obtain a solid product with a residual moisture content of 4 to 8% and the solid product was finely ground with sugar, starch or modified starch to obtain a pourable product.

* * * * *